United States Patent [19]

Nilsen et al.

[11] 4,166,602
[45] Sep. 4, 1979

[54] COUNTERBALANCING MECHANISM FOR X-RAY TUBEHEADS

[75] Inventors: Carl G. Nilsen, Lincroft; Richard A. Gabel, Livingston, both of N.J.

[73] Assignee: Pennwalt Corporation, Philadelphia, Pa.

[21] Appl. No.: 907,226

[22] Filed: May 18, 1978

[51] Int. Cl.² ............................. B66D 1/00; A47F 5/00
[52] U.S. Cl. .............................. 248/280.1; 248/123.1; 248/324
[58] Field of Search .................. 248/324, 325, 123, 124, 248/122, 278, 280, 281, 16, 54 R

[56] References Cited

U.S. PATENT DOCUMENTS

| | | | |
|---|---|---|---|
| 1,638,938 | 8/1927 | Koenigkramer | 248/281 X |
| 2,287,577 | 6/1942 | Stava | 248/280 |
| 3,000,606 | 9/1961 | Storm et al. | 248/281 X |
| 3,883,105 | 5/1975 | Matsumoto | 248/281 |
| 3,917,200 | 11/1975 | Johnson | 248/280 X |
| 4,082,244 | 4/1978 | Groff | 248/280 |

Primary Examiner—J. Franklin Foss

[57] ABSTRACT

An X-ray tubehead counterbalancing mechanism devoid of springs, cams and chains is disclosed. The mechanism requires only a single adjustment to precisely counterbalance objects, such as tubeheads and the like. The mechanism includes a commercially available gas spring which is used in conjunction with parallel motion linkage assembly which carries the tubehead. The piston rod end of the gas spring is adjustable upwardly or downwardly in a direction substantially normal to the axis of the piston rod by means of a single adjustment screw cooperating with a clevis which pivotally mounts the piston rod. With such adjustment capability, the present mechanism will support and counterbalance tubeheads having wide variations in weight and inertia.

6 Claims, 9 Drawing Figures

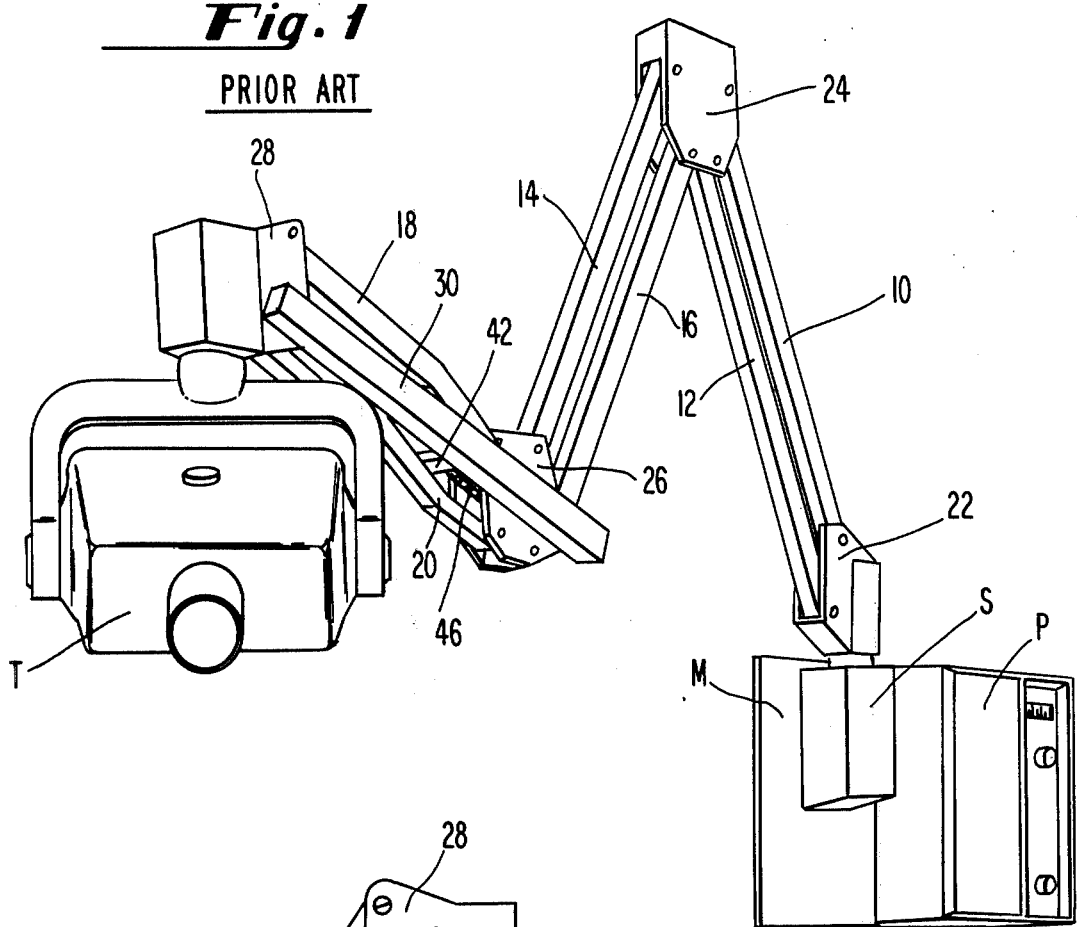
Fig. 1 PRIOR ART
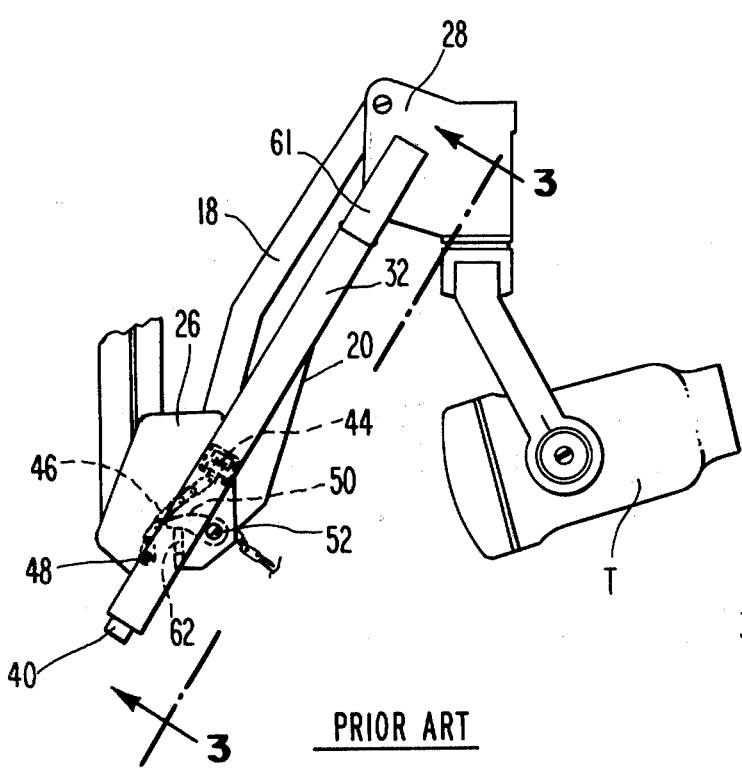
Fig. 2 PRIOR ART
Fig. 3 PRIOR ART

COUNTERBALANCING MECHANISM FOR X-RAY TUBEHEADS

STATEMENT OF THE INVENTION

This invention relates to X-ray equipment and more particularly to gas spring means for counterbalancing X-ray tubeheads.

BACKGROUND OF THE INVENTION

Counterbalancing means are required to support the weight of the X-ray tubehead as well as to maintain the tubehead in a desired position after it has been moved thereto. Several prior art mechanisms for accomplishing such tubehead counterbalancing employ spring means to counterbalance the tubehead in an upper position and include an arrangement for increasing the resistance of the spring means in lowered positions where additional force is necessary in order to achieve effective counterbalancing.

Other mechanisms employ a plurality of springs. One of the springs however would only be brought into action in lower positions of the tubehead, thus providing substantially uniform counterbalancing of the tubehead in almost any position.

Still other prior art mechanisms employ cam-chain arrangements in addition to spring means. A chain is caused to slide over a cam or roller surface in response to movement of the tubehead to change the tension of the springs in order to compensate for the change in moment of the parallel motion linkage arms associated with the counterbalance mechanism as the tubehead is moved from one position to another.

Each of the abovediscussed prior art mechanisms is somewhat cumbersome, complicated to use, and quite expensive to fabricate. Further, if tubeheads of different weights are to be effectively counterbalanced, then at least two separate adjustments, and even three, must be made by the dentist prior to actual use of the tubehead.

SUMMARY OF THE INVENTION

The counterbalance mechanism of the present invention is characterized by an absence of cams, chains or springs, and yet permits tubeheads having wide weight and inertia variations to be accurately counterbalanced through the simple expediency of turning a single adjustment screw.

The invention employs a commercially available gas spring disposed in close proximity to the tubehead. The gas spring is used in conjuntion with parallel motion linkage assembly which carries the tubehead and provides a substantially uniform force which opposes the weight of the tubehead throughout the expected range of tubehead travel.

BRIEF DESCRIPTION OF THE DRAWINGS

FIG. 1 a perspective view of an X-ray arm and tubehead assembly with existing counterbalancing means therefore.

FIG. 2 is a partially sectioned, longitudinal view of the counterbalance mechanism shown in FIG. 1.

FIG. 3 is a view, partially sectioned, parts omitted for clarity, of the counterbalance mechanism of FIG. 2 taken substantially along line 3—3 thereof.

DESCRIPTION OF A PRIOR ART EMBODIMENT

Figure 5:
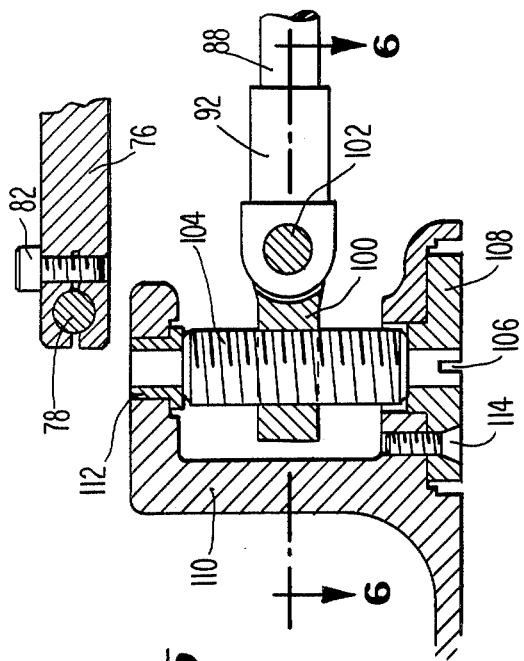
FIG. 5 is a fragmentary sectional view of the adjustment means of the counterbalancing mechanism of FIG. 4, taken substantially along line 5—5 thereof, the adjustment means being shown in an intermediate position.
Figure 5:
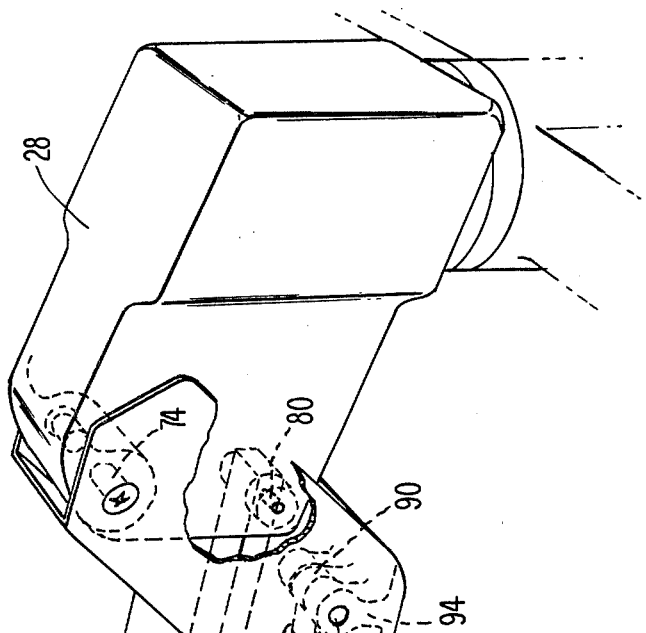

In order to more fully appreciate the present invention, an existing X-ray tubehead counterbalancing mechanism of the present assignee will be described, which mechanism is modified in accordance with the invention.

Referring to FIGS. 1, 2 and 3, a tubehead T is carried by an X-ray arm assembly comprising 3 pairs of arms, 10, 12; 14, 16; and 18, 20, forming parallel motion linkages of known operation. Arms 10 and 12 are pivotally mounted between a knuckle assembly 22 and triangle assembly 24. The other pairs of arms are similarly respectively mounted between triangle assembly 24 and cam housing 26, and cam housing 26 and trunnion 28. Arms 10 and 12 move in conjunction with arms 14 and 16 through interconnecting gear segments contained within triangle assembly 24.

A wall plate mounting M mounts a control panel P and a member S which supports the X-ray assembly and permits its lateral rotation.

Pivotally mounted to trunnion 28 is a counterbalance assembly 30 which serves to facilitate positioning of tubehead T and to stabilize the tubehead at a desired position.

Counterbalance assembly 30 (FIGS. 2 and 3) comprises a pair of identical spring holder tubes 32, each disposed at an opposite side of arm 20 in parallel relationship thereto. Each spring holder tube 32 contains a tension spring 34. A tensioning rod 36 is fastened to the inner end of each spring 34. Each tensioning rod 36 cooperates with an adjustment screw 38 which may be rotated in either direction by means of an adjusting knob 40. For clarity of understanding, the inner ends of springs 34 are designated those ends which are proximal to cam housing 26 and distal from trunnion 28.

Spring holder tubes 32 are rigidly interconnected by a bar member 42 which carries a yoke member 44 to which one end of chain 46 is pivotally attached, its other end being fastened to a pivot pin 48 mounted to cam housing 26. Chain 46 contacts a cam 50, pivotally-mounted to cam housing 26 by means of a pivot pin 52. Coaction between cam 50 and chain 46 is later described.

A pivot block 54 articulates with each outer end of springs 34 through rods 56. Pivot blocks 54 are pivotally connected to arm 20 through a pivot shaft 58 and spacers 60. Spring holder tubes 32 therefore are capable of pivotal motion about outer end of arm 20.

Thus, rotation of adjustment screws 38 in one direction through adjusting knobs 40 will increase the length of springs 34 to thereby increase their tension which will permit a heavier tubehead to be counterbalanced. Conversely, rotation of knobs 40 in the other direction will permit counterbalancing of a lighter weight tubehead.

Cam 50 may be adjusted by means of an adjustment screw 62 mounted through an underside of cam housing 26. By turning adjustment screw 62, cam 50 is caused to pivot about pivot pin 52 to change the tension of springs 34. Thus, movement of tubehead T to another position will cause one or more links of chain 46 to contact or slide over cam 50 to thereby exert an increasing or decreasing force on bar member 42, which change in force is then transmitted to arm 20 and trunnion 28 through pivot blocks 54 acting through rods 56 on springs 34. In accordance with the above, springs 34 will be extended when tubehead T is lowered.

It is apparent from the foregoing description that a cam, chain, and springs are required to counterbalance tubeheads having weight variations exceeding the counterbalance support of the counterbalance assembly. Further, three separate adjustments are needed to adjust such assembly, i.e., two adjustment knobs 40 and cam adjustment screw 62.

DETAILED DESCRIPTION OF THE INVENTION

Figure 4:
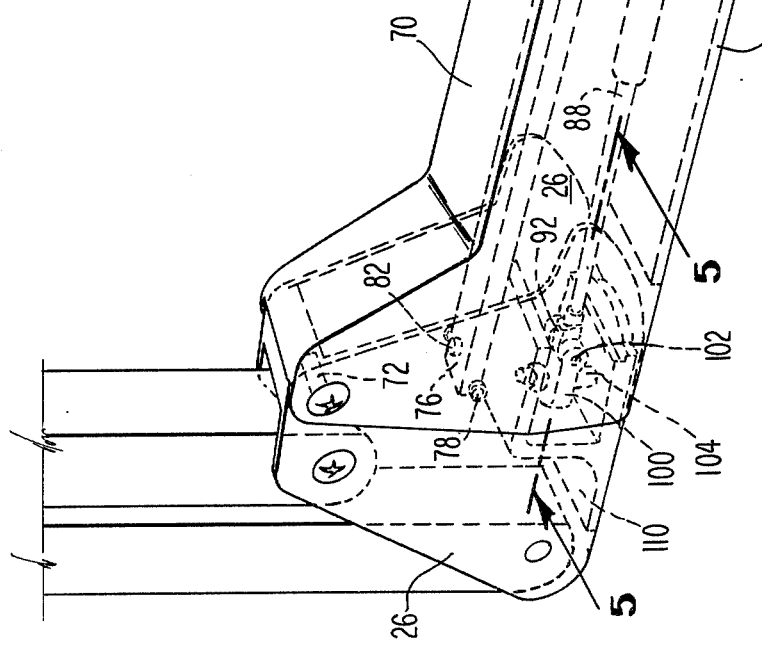
FIG. 4 is a cutaway perspective view of the counterbalancing mechanism of the present invention.
Figure 6:
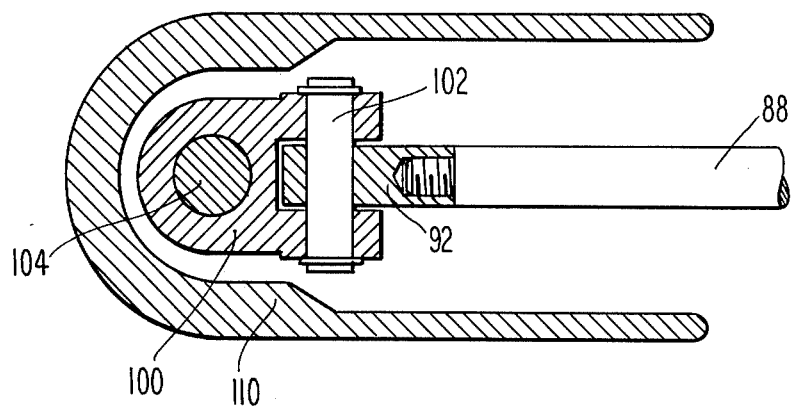
FIG. 6 is sectional view of the adjustment means shown in FIG. 5 taken along line 6—6 thereof.

Referring to FIGS. 4, 5 and 6, a hollow casting 70, suitably aluminum, is pivotally mounted to cam housing 26 and trunnion 28 through pivot pins 72 and 74 respectively. A stabilizer bar 76 is disposed within casting 70 although not in direct contact therewith. Stabilizer bar 76 is pivotable on cam housing 26 and trunnion 28 by means of pivot pins 78 and 80 respectively. In order to preclude any relative movement between stabilizer bar 76 and either of the pivot pins 78 or 80, a clamping screw 82 is provided at each end of stabilizer bar 76. When so clamped, stabilizer bar 76 assists in stabilizing the vertical attitude of the tubehead.

A commercially available gas spring comprises a cylinder 86 and cooperating piston rod 88, each being provided with a suitable end fitting 90 and 92 respectively. The gas spring is disposed within casting 70 below stabilizer bar 76. Cylinder 86, through end fitting 90, is pivotally secured to yoke 94 through pivot pin 96. Yoke 94 may conveniently be formed integrally with casting 70. End fitting 92 pivots within a clevis member 100 through pivot pin 102. Clevis 100 is internally threaded to receive adjustment screw 104 which may be rotated in either direction when a suitable tool engages slot 106. Adjustment screw retainer plate 108, housing 110, and bushing 112 maintain adjustment screw 104 normal to base 113 of casting 70. Retainer plate 108 and housing 110 are secured together by means of screws 114. Housing 110 may be formed as part of casting 70.

Figure 7:
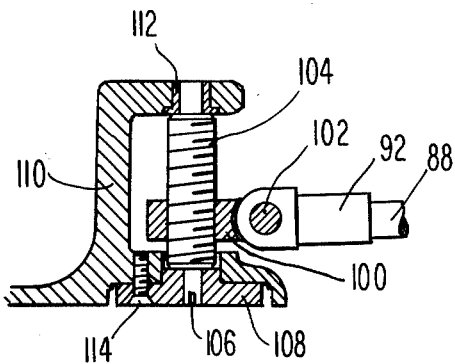
FIGS. 7 and 8 are views of the adjustment means, similar to FIG. 5, but illustrating such means in a lower and upper adjustment position respectively.
Figure 8:
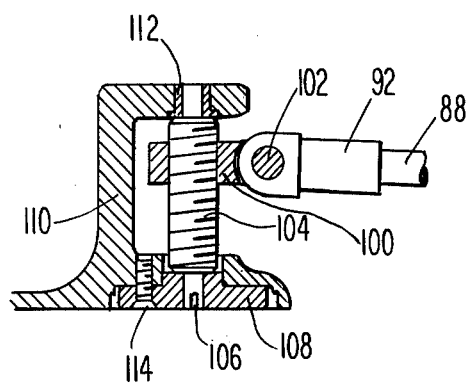

FIGS. 7 and 8 show piston rod 88 in a lower and upper adjustment position respectively. If the centers of pivot pins 102 and 72 (FIG. 4) are designated points A and B respectively, it can be shown, as distance AB is shortened when clevis 100 moves upwardly, that objects of lesser weight will be supported by the present counterbalancing mechanism. That is, as point A is adjusted upwardly or downwardly to change the length of the resisting moment arm AB, the capacity of the counterbalancing mechanism to support different tubehead weights is accordingly adjusted.

Figure 9:
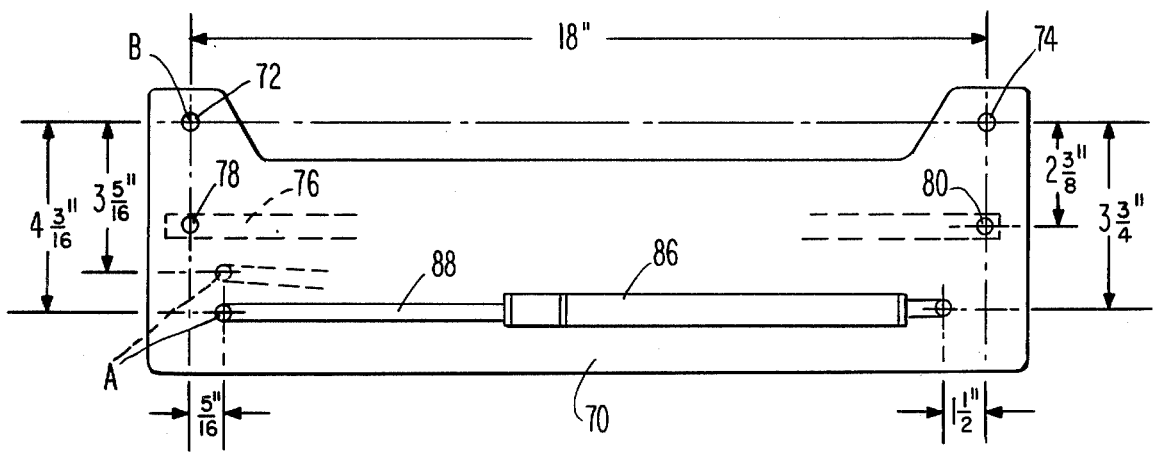
FIG. 9 is a diagrammatic representation of an embodiment of the present invention with illustrative dimensions and limitations.

More specifically, reference is now made to FIG. 9 wherein specific values for a given system is present, and wherein the arm or casting 70 forms an angle with the horizontal between +35° and −35°. As the distance AB is increased from 3 5/16 inches to 4 3/16 inches, tubehead weights in the approximate range of 42 lbs. to 51 lbs. are effectively counterbalanced. It will be appreciated that the present counterbalancing mechanism is capable of providing precise balance over the full range aforementioned by merely rotating adjustment screw 104 carefully in the desired direction. Force diagram slopes for gas springs are obtainable from the manufacturer.

The invention is not limited to the specific values stated in FIG. 9, it being understood that dimensions other than shown as well as gas spring characteristics differing from the abovementioned may be used advantageously with the present invention and that a skilled mathematician can calculate the necessary parameters which will effectively counterbalance objects of different weights in light of the teachings of the present invention.

We claim:

1. In an extensible and adjustable X-ray arm carrying an X-ray tubehead at an outer end thereof, said X-ray arm including a linkage assembly articulating successively between each of a knuckle assembly, triangle assembly, cam housing assembly, and trunnion assembly, said tubehead communicating with said trunnion assembly and having wide weight and inertia variations, the combination therewith of the improvement for precisely counterbalancing said tubehead by means of a single adjustment, said counterbalancing being achieved by a counterbalance mechanism devoid of cams, chains and springs and comprising
   a hollow structural member pivotally connected at upper end portions thereof to said cam housing assembly and trunnion assembly,
   a gas spring disposed at a lower portion of said hollow structural member, said gas spring including a cylinder and a piston rod,
   means within said hollow structural member for pivotally mounting said cylinder proximal to pivotal connection of said structural member to said trunnion assembly, and
   other means within said structural member for moving outer end of said piston rod in a direction substantially normal to axis of said gas spring for changing resisting moment arm to counterbalance said tubehead.

2. The counterbalancing mechanism of claim 1 wherein said other means comprises
   an adjustment screw,
   means for maintaining said adjustment screw substantially normal to axis of said gas spring, and
   additional means secured to said outer end of said piston rod responsive to rotation of said adjustment screw.

3. The counterbalancing mechanism of claim 2 wherein said adjustment screw is rotated in a direction which shortens distance between said additional means and pivotal connection of said structural member to said cam housing assembly for permitting said counterbalancing mechanism to counterbalance a tubehead of lighter weight.

4. The counterbalancing mechanism of claim 2 wherein said adjustment screw is rotated in a direction which increases distance between said additional means and pivotal connection of said structural member to said cam housing assembly for permitting said counterbalancing mechanism to counterbalance a tubehead of greater weight.

5. The counterbalancing mechanism of claim 2 wherein said additional means comprises
   an internally threaded clevis responsive to rotation of said adjustment screw,
   an end fitting secured to said outer end of said piston rod, and
   means for pivoting said end fitting within said clevis.

6. The counterbalancing mechanism of claim 2 further characterized by a stabilizer bar disposed within said structural member above said gas spring,
   said stabilizer bar being pivotally connected to said cam housing assembly and said trunnion assembly for stabilizing vertical attitude of said tubehead.

* * * * *